| United States Patent [19] | [11] 3,962,310 |
| Li et al. | [45] June 8, 1976 |

[54] AMMOXIDATION PROCESS

[75] Inventors: Tao P. Li, Chesterfield; Charles W. Hobbs, St. Charles, both of Mo.

[73] Assignee: Monsanto Company, St. Louis, Mo.

[22] Filed: Dec. 30, 1974

[21] Appl. No.: 537,495

Related U.S. Application Data

[62] Division of Ser. No. 320,373, Jan. 2, 1973.

[52] U.S. Cl. ........................ 260/465.3; 260/604 R; 260/669 R; 260/680 C
[51] Int. Cl.² ........................................ C07C 120/14
[58] Field of Search ................................ 260/465.3

[56] References Cited
UNITED STATES PATENTS

| 3,338,952 | 8/1967 | Callahan et al. .................. 260/465.3 |
| 3,431,292 | 3/1969 | Callahan et al. .................. 260/465.3 |
| 3,849,337 | 11/1974 | Manara et al. .................... 260/465.3 |

FOREIGN PATENTS OR APPLICATIONS

| 1,007,929 | 10/1965 | United Kingdom ............. 260/465.3 |

*Primary Examiner*—Joseph P. Brust
*Attorney, Agent, or Firm*—Elizabeth F. Sporar

[57] ABSTRACT

Olefins, such as propylene, are oxidized to form acrolein and ammoixidized to form acrylonitrile in the presence of a catalyst containing the elements antimony, uranium, iron and bismuth in a catalytic active oxidized state.

4 Claims, No Drawings

AMMOXIDATION PROCESS

CROSS REFERENCE TO RELATED APPLICATION

This application is a division of copending application Ser. No. 320,373 filed Jan. 2, 1973.

BACKGROUND OF THE INVENTION

This invention relates to an improved oxidation and/or ammoxidation catalyst system containing the elements antimony, uranium, iron and bismuth and to a method for preparing such catalyst system.

It is well known that olefins can be oxidized to oxygenated hydrocarbons such as unsaturated aldehydes and acids, for example, acrolein and methacrolein, acrylic and methacrylic acid. It is also well known that olefins can be ammoxidized to unsaturated nitriles such as acrylonitrile and methacrylonitrile. The value of such oxygenated hydrocarbons and unsaturated nitriles is generally well recognized with acrylonitrile being among the most valuable monomers available to the polymer industry for producing useful polymeric products.

Various catalytic processes are known for the oxidation and/or ammoxidation of olefins. Such processes commonly react an olefin or an olefin-ammonia mixture with oxygen in the vapor phase in the presence of a catalyst. For the production of acrolein and acrylonitrile, propylene is the generally used olefin reactant and for the production of methacrolein and methacrylonitrile, isobutylene is the generally used olefin reactant.

A catalyst system composed of the oxides of antimony and uranium and the oxidation and ammoxidation of olefins using such catalyst has been described in U.S. Pat. Nos. 3,198,750 and 3,308,151. These patents describe preparation of the catalyst by precipitation wherein the oxides of the elements are contained in a slurry which is filtered to remove soluble salts and recover the catalytic components as the filter cake.

In the catalytic oxidation and/or ammoxidation of olefins, the commercial utility of a catalyst system is highly dependent upon the cost of the system, the conversion of the olefin and the yield of the desired product. In many cases a reduction in the cost of a catalyst system in the order of a few pennies per pound or a 1% increase in the yield of a desired product represents a tremendous commercial economical savings. Accordingly, research efforts are continuously being made to define new or improved catalyst systems and methods of making new and old catalyst systems to reduce the cost and/or to upgrade the activity and selectivity of such catalyst systems in particular processes.

SUMMARY

This invention is directed to an improved catalyst system containing the elements antimony, uranium, iron and bismuth having commercial activity and selectivity for the catalytic oxidation and/or ammoxidation of olefins and to an improved method of making such catalyst system.

Accordingly, typical objects of this invention are to provide: (1) an improved oxidation and/or ammoxidation catalyst system containing oxygen, antimony, uranium, iron and bismuth, (2) an improved process for the preparation of a catalyst system containing oxygen, antimony, uranium, iron and bismuth, and (3) an improved olefin conversion process.

Other objects, aspects and advantages of this invention will become apparent to those skilled in the art upon further study of this disclosure and the appended claims.

In accordance with this invention, a new oxidation/ammoxidation catalyst system based on the elements antimony, uranium, iron and bismuth is provided. The elements are in combination with oxygen and may exist as individual oxides or as complexes of two or more of the elements and oxygen or as a combination of oxides and complexes. The atomic ratio of the elements present in the catalyst system may vary over a wide range. Generally speaking the catalyst may be defined by the following empirical formula:

$Sb_aU_bFe_cBi_dO_e$ wherein $a$ is 1 – 10, $b$ is 0.01 to 1, $c$ is 0.01 to 1, $d$ is 0.001 to 0.1 and $e$ is a number taken to satisfy the average valences of the Sb, U, Fe and Bi in the oxidation states in which they exist in the catalyst.

The catalyst can be prepared starting with individual oxides or sulfates of the elements. A preferred method of preparing the catalyst is to combine the oxides or sulfates of the elements with sulfuric acid. When antimony sulfate is used as a starting material, it can be added to water wherein sulfuric acid is obtained. Nitric acid is used to oxidize the sulfate salts of the elements or to further oxidize the oxides of the elements. After the acid mixture has digested, the pH of the mixture is adjusted to about 8 followed by filtration.

After filtering the mixture, the filter cake can be dried at a temperature of from about 100°C to about 180°C. A suitable drying temperature is about 110°C. However, the drying can be obtained at higher temperatures such as up to about 650°C. The time required for drying the filter cake can range from an hour up to about 64 hours. Obviously, the drying temperature selected will dictate the required drying time with the lower temperature requiring the longer time. Also, the filter cake may be dried at different temperatures, for example at 110°C for from 2 to 64 hours and then at a temperature of from about 250°C to about 650°C for from 2 to 24 hours.

After the filter cake is dried, it is further heated at an elevated temperature to obtain the active catalytic form of the elements. This calcination of the catalyst is conducted at a temperature in the range of from about 500°C to about 1150°C. The time for calcination can vary and depends upon the temperatures employed. Generally, a time period of 2 to 24 hours at the designated temperatures is sufficient. The calcination may be conducted in the presence of oxygen (air); however, the catalyst may also be made active by calcining it in the absence of oxygen, such as in a nitrogen atmosphere.

The catalyst can be employed without support, and will display excellent activity. It also can be combined with a support, and preferably at least 5% up to about 90% preferably 5 to 50%, of the supporting compound by weight of the entire composition is employed in this event. Any known support materials can be used, such, for example, silica, alumina, zirconia, alundum, silicon carbide, alumina-silica, and the inorganic phosphates, silicates, aluminates, borates and carbonates stable under the reaction conditions to be encountered in the use of the catalyst.

The improved catalyst of this invention exhibits exceptional utility in the conversion of olefins with or without the presence of ammonia. The olefins employed as reactants for conversion by the catalyst of this invention may be open chain as well as cyclic and include, for example, propylene, butene-1, butene-2, isobutene, pentene-1, pentene-2, 3-methyl butene-1, 2-methyl butene-2, hexene-1, hexene-2, 4-methyl pentene-1, 3,3 dimethyl butene-1, 4-methyl pentene-2, octene-1, cyclopentene, cyclohexene, and the like. Particularly, when the catalyst of this invention is used as merely an oxidation catalyst, it is particularly adapted to the conversion of propylene to acrolein and isobutylene to methacrolein. Of course, mixtures of olefins may be employed and mixtures of olefins with other hydrocarbons are applicable to the process of this invention. When the catalyst of this invention is to be used as an ammoxidation catalyst, the olefins as aforestated are applicable. However, the catalyst of this invention is particularly adapted to the conversion of propylene with ammonia and oxygen to acrylonitrile at 250°C to 650°C.

The molar ratio of oxygen to the olefin in the feed will generally be in the range of 0.5:1 to 4:1 with a preferred ratio being 1:1 to 3:1. The molar ratio of ammonia to olefin in the feed will generally be in the range of 0.5:1 to 5:1 and preferably slightly over the stoichiometric ratio of 1:1 ammonia-olefin will be employed.

While ammonia is most generally employed as the nitrogen providing compound, other nitrogen containing materials may be employed which decompose to produce reactive nitrogen under the reaction conditions. Any source of oxygen, pure or in admixture with inerts, may be employed in the process of this invention. Air is a satisfactory source of oxygen for use in this invention.

The catalyst system of this invention can be advantageously employed for synthesizing styrene from ethylbenzene and oxygen, butadiene from butenes and oxygen, acrolein or methacrolein from propylene or isobutylene and oxygen, acrylonitrile or methacrylonitrile from propylene or isobutylene, ammonia and oxygen, isoprene from 2-methyl butene-2 and oxygen, and 2-cyano-1,3-butadiene from 2-methyl butene-2 or isoprene, ammonia and oxygen.

DESCRIPTION OF PREFERRED EMBODIMENTS

The following Examples are presented as illustrative of the invention and, as such, are not intended to be restrictive upon the specific materials, quantities and operation variables specifically set forth therein.

As used in the examples, the following terms have the following definitions:

$$\% \text{ propylene } (C_3H_6) \text{ converted} = \frac{\text{mols } C_3H_6 \text{ in feed} - \text{mols } C_3H_6 \text{ in effluent}}{\text{mols } C_3H_6 \text{ in feed}} \times 100$$

$$\% \text{ propylene to acrylonitrile} = \frac{\text{moles AN formed}}{\text{mols } C_3H_6 \text{ in feed}} \times 100$$

The apparatus employed in carrying out the runs in this example is a fluidized bed type reactor. The reactor consists of a 14 mm. inside diameter 96% quartz glass tube fitted at the bottom with a fritted disc for supporting a catalyst bed of up to 50 ml. in volume and fitted at the top with another fritted disc to remove entrained catalyst from the reactor effluent. A thermowell of 4 mm. outside diameter 96% quartz glass extends through the center of the catalyst bed to the fritted disc. The reactor tube is jacketed with a larger tube in which sand is fluidized for providing even heat distribution. The entire reactor assembly is placed in a controlled, hinged tube furnace. The reactant gases are premixed and heated to about 470°C before entering the bottom of the reactor through a single inlet tube. The effluent gases from the reactor are heated to prevent condensation prior to chromatographic analysis.

EXAMPLE I

Five catalyst systems composed of antimony, uranium, iron and bismuth are prepared by adding antimony, uranium and bismuth oxides and iron sulfate to 290 ml. of water to which is then added 83 grams of 98% $H_2SO_4$. The mixture is stirred for about 3 hours at a temperature of 80°C. Nitric acid is added to the mixture which is then stirred for two hours to further oxidize the elements. After cooling the mixture the pH is adjusted to about 8 with ammonium hydroxide. The mixture is allowed to digest about 16 hours. After digestion the mixture is filtered and the precipitate is washed with water. The precipitate is mixed with silica sol (Ludox AS) and the mixture is evaporated to dryness and further dried at about 110°C for about 16 hours. The resulting catalyst is calcined at 500°C for 1 hour, then at 700°C for 1 hour and then at 900°C for 12 hours. The quantities of the various components used in making catalyst systems are given in the following Table I.

TABLE I

| COMPONENT | CAT.A | CAT.B | CAT.C | CAT.D | CAT.E |
|---|---|---|---|---|---|
| $Sb_2O_3$ (grams) | 65.5 | 54.5 | 54.5 | 109 | 109 |
| $U_3O_x$ (grams) | 14.0 | 14.0 | 14.0 | 28.0 | 28.0 |
| $FeSO_4.7H_2O$ (grams) | 27.8 | 27.8 | 27.8 | 55.6 | 55.6 |
| $Bi_2O_3$ | 1.4 | 0.7 | 0.7 | 1.4 | 1.4 |
| Silica sol (Ludox AS) (grams) | 107.0 | 121.0 | 121.0 | 242 | 242 |
| ATOMIC RATIO | | | | | |
| Sb/U/Fe/Bi | 3:0.33: 0.66: 0.04 | 2.5:0.33: 0.66: 0.02 | 2.5:0.33: 0.66: 0.02 | 2.5:0.33: 0.66: 0.02 | 2.5:0.33: 0.66: 0.02 |

TABLE I-continued

| COMPONENT | CAT.A | CAT.B | CAT.C | CAT.D | CAT.E |
|---|---|---|---|---|---|
| $SiO_2$ % | 25 | 30 | 30 | 30 | 30 |
| CALCINATION | | | | | |
| Hours – Temp. (°C) | 1–500 | 1–500 | 1–500 | 1–500 | 1–500 |
| | 1–700 | 1–700 | 1–700 | 1–700 | 1–700 |
| | 12–900 | 12–950 | 6–900 | 12–850 | 12–900 |
| | | | | 12–900 | 10–950 |
| | | | | 10–950 | |

EXAMPLE II

Three catalyst systems made according to the general procedure of Example I are used in the conversion of propylene and ammonia to acrylonitrile using the apparatus previously described. The feed composition in these comparative runs is 8.9% ammonia, 8.5% propylene, 17.5% oxygen and 65.1% helium.

In each run the temperature is about 490°C and the pressure is varied. Other process data and the results are given in Table II. The catalysts are identified as:

A — $Sb_3U_{0.33}Fe_{0.66}$ — 25% $SiO_2$
B — $Sb_{2.5}U_{0.33}Fe_{0.66}Bi_{0.02}$ — 30% $SiO_2$
C — $Sb_{2.5}U_{0.33}Fe_{0.66}Bi_{0.04}$ — 30% $SiO_2$

TABLE II

| Catalyst | A | | B[1] | | C | |
|---|---|---|---|---|---|---|
| Catalyst Weight (grams) | 30 | 30 | 30 | 30 | 30 | 30 |
| Pressure (psig) | 0.6 | 18 | 1 | 18.2 | 1 | 18 |
| Contact Time* (gm.sec/ml.) at STP | 5 | 5 | 6 | 6 | 6 | 6 |
| Elapsed Reaction (min) | 65 | 215 | 35 | 155 | 65 | 185 |
| Percent Propylene Converted | 88.9 | 94.9 | 92.9 | 95.9 | 90.4 | 94.8 |
| Percent Propylene to Acrylonitrile | 71.3 | 65.6 | 78.9 | 73.9 | 71.9 | 66.9 |
| Stability | S | U | S | S | S | S |

S - Stable
U - Unstable

[1] reaction temperature of 465°C

*Contact time determined as $\frac{\text{Weight of Catalyst (grams)}}{\text{Feed Flow Rate (ml./sec.) at STP}}$ The above example shows the improved ammoxidation activity of the four component catalyst system of this invention compared with three component catalysts and the stability and the improvement of acrylonitrile yield of the four component system under pressure operation.

EXAMPLE III

Two catalyst systems made according to the general procedure of Example I are used in the conversion of propylene and ammonia to acrylonitrile using the apparatus previously described. The feed composition in these comparative runs is 8.9% ammonia, 8.5% propylene, 17.5% oxygen and 65.1% helium. In each run the temperature is about 490°C, 30.0 grams of catalyst is used and the contact time is 6 gm.sec./ml (at STP). Other process data and the results are given in Table III. The catalysts are identified as:

A — $Sb_{2.5}U_{0.33}Fe_{0.66}Bi_{0.04}$ — 30% $SiO_2$
B — $Sb_3U_{0.33}Fe_{0.66}Bi_{0.04}$ — 25% $SiO_2$

TABLE III

| Catalyst | A | | B | |
|---|---|---|---|---|
| Pressure (psig) | 1 | 18.5 | 1 | 18.5 |
| Percent Propylene Converted | 89.9 | 95.1 | 86.8 | 92.9 |
| Percent Propylene to Acrylonitrile | 71.7 | 66.6 | 70.5 | 65.6 |

*Contact time determined as $\frac{\text{Weight of Catalyst (grams)}}{\text{Feed Flow Rate (ml./sec.) at STP}}$ The above example shows that various atomic ratios of antimony in the catalyst system of this invention are useful.

EXAMPLE IV

The catalyst systems of Example I are used in the conversion of isobutylene to methacrylonitrile using the apparatus previously described. Methacrylonitrile is obtained using each catalyst with a feed composition of 8.9% ammonia, 8.5% isobutylene, 17.5% oxygen and 65.1% helium, all on a volume basis, at a temperature of 500°C and atmospheric pressure.

EXAMPLE V

The catalyst systems of Example I are used in the conversion of propylene to acrolein using the apparatus previously described. Acrolein is obtained using each catalyst with a feed composition of 7.0% propylene, 11% oxygen and 82% helium, all on a volume basis, at a temperature of 500°C and atmospheric pressure.

From the foregoing example it will be clearly noted that the catalyst system of this invention exhibits activity, selectivity and stability when used at elevated pressures.

It will be obvious to persons skilled in the art that various modifications may be made in the improved catalyst and process as described in this application. Accordingly, it is intended that all such modifications which reasonably fall within the scope of the appended claims are a part hereof.

What is claimed is:

1. A process for producing acrylonitrile or methacrylonitrile which comprises reacting in the vapor phase an olefin selected from the group consisting of propylene and isobutylene with ammonia and oxygen in amounts such that the molar ratio of ammonia to olefin is in the range from about 0.5:1 to about 5:1 and the molar ratio of olefin to oxygen is in the range from about 0.5:1 to 4:1, at a temperature in the range from about 250° to 650°C in contact with a catalyst system consisting essentially of the elements antimony, uranium, iron and bismuth in an oxidized state represented by the formula $$Sb_a U_b Fe_c Bi_d O_e$$

wherein $a$ is 1–10, $b$ is 1–10, $c$ is 0.01–1, $d$ is 0.001–0.1 and $e$ is a number taken to satisfy the average valences of the Sb, U, Fe and Bi in their catalytic active oxidation states prepared by forming a mixture of oxides or sulfates of antimony, uranium, iron and bismuth in sulfuric acid, oxidizing said mixture with nitric acid, digesting the resulting mixture, adjusting the pH to about 8, filtering the mixture, mixing the filter cake with a catalyst support and evaporating the filter cake mixture to dryness, then heating the dried mixture at a temperature of from about 500° to about 1150°C to form said active oxidation states.

2. The process of claim 1 wherein said mixture is formed from $Sb_2O_3$, $U_3O_8$, $Bi_2O_3$ and $FeSO_4.7H_2O$.

3. The process of claim 1 wherein the support is silica.

4. The process of claim 3 wherein the olefin is propylene.

* * * * *